(12) United States Patent
Iyer et al.

(10) Patent No.: US 7,335,786 B1
(45) Date of Patent: Feb. 26, 2008

(54) MICHAEL-ADDUCT FLUOROCHEMICAL SILANES

(75) Inventors: Suresh Iyer, Woodbury, MN (US);
Oscar S. Benz, Minneapolis, MN (US);
Thomas P. Klun, Lakeland, MN (US);
Wayne W. Fan, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/693,510

(22) Filed: Mar. 29, 2007

(51) Int. Cl.
*C07F 7/04* (2006.01)

(52) U.S. Cl. .................................................. 556/485

(58) Field of Classification Search ................. 556/485
See application file for complete search history.

(56) References Cited

U.S. PATENT DOCUMENTS

| | | | |
|---|---|---|---|
| 3,250,807 A | 5/1966 | Fritz et al. | |
| 3,250,808 A | 5/1966 | Moore, Jr. et al. | |
| 3,493,424 A | 2/1970 | Mohrlok et al. | |
| 3,810,874 A | 5/1974 | Mitsch et al. | |
| 4,262,072 A | 4/1981 | Wendling et al. | |
| 4,321,404 A | 3/1982 | Williams et al. | |
| 4,348,462 A | 9/1982 | Chung | |
| 4,351,736 A | 9/1982 | Steinberger et al. | |
| 4,378,250 A | 3/1983 | Treadway et al. | |
| 4,508,916 A | 4/1985 | Newell et al. | |
| 4,781,844 A | 11/1988 | Kortmann et al. | |
| 4,873,140 A | 10/1989 | McIntyre | |
| 5,073,442 A | 12/1991 | Knowlton et al. | |
| 6,183,872 B1 | 2/2001 | Tanaka et al. | |
| 6,277,485 B1 | 8/2001 | Invie et al. | |
| 6,923,921 B2 | 8/2005 | Flynn et al. | |
| 6,991,826 B2 | 1/2006 | Pellerite et al. | |
| 7,094,829 B2 | 8/2006 | Audenaert et al. | |
| 7,101,618 B2 | 9/2006 | Coggio et al. | |
| 2004/0077775 A1 | 4/2004 | Audenaert et al. | |
| 2004/0253369 A1 | 12/2004 | Jallouli et al. | |
| 2005/0054804 A1 | 3/2005 | Dams et al. | |
| 2005/0249940 A1 | 11/2005 | Klun et al. | |
| 2005/0250298 A1 | 11/2005 | Bauer | |
| 2005/0250921 A1 | 11/2005 | Qiu et al. | |
| 2006/0216500 A1 | 9/2006 | Klun et al. | |

FOREIGN PATENT DOCUMENTS

WO    WO 01/68384    9/2001

OTHER PUBLICATIONS

Kawashiro, Katsuhiro, et al., Gas Chromatography-Mass Spectrometry of N-Trifluoroacetyl Trimethylsilyl Esters of Some Iminodicarboxylic Acids, (1985), 58, 2727-2728.*
Mather, B.D., et al., "Michael addition reactions in macromolecular design for emerging technologies", *Prog. Polym. Sci.*, (2006) vol. 31, No. 5, pp. 487-531.
U.S. Appl. No. 11/277,162 entitled Perfluoropolyether Urethane Additives having (Meth)acryl Groups and Hardcoats filed Mar. 22, 2006.
U.S. Appl. No. 60/871,034 entitled "Fluorochemical Urethane Compounds Having Pendent Silyl Groups" filed Dec. 20, 2006.
U.S. Appl. No. 11/683,823 entitled "Fluorochemical Compounds Having Pendent Silyl Groups" filed Mar. 8, 2007.

* cited by examiner

*Primary Examiner*—Yvonne Eyler
*Assistant Examiner*—Jennifer Y Cho
(74) *Attorney, Agent, or Firm*—Kent S. Kokko

(57) ABSTRACT

Fluorochemical silane compounds and coating compositions derived therefrom are described. The compounds and compositions may be used in treating substrates, in particular substrates having a hard surface such as ceramics or glass, to render them water, oil, stain, and soil repellent.

20 Claims, No Drawings

MICHAEL-ADDUCT FLUOROCHEMICAL SILANES

FIELD OF THE INVENTION

The present invention relates to fluorochemical silane compounds and coating compositions derived therefrom, which may be used in treating substrates, in particular substrates having a hard surface such as ceramics or glass, to render them water, oil, stain, and soil repellent, and for treating antireflective substrates, such as optical lenses.

BACKGROUND

Although many fluorinated compositions are known in the art for treating substrates to render them oil and water repellent, there continues to be a desire to provide further improved compositions for the treatment of substrates, in particular substrates having a hard surface such as ceramics, glass and stone, in order to render them water-repellent, oil-repellent, and easy to clean. There is also a need for treating glass and plastic as a hard surface, particularly in the optical field, in order to render them stain, dirt and dust resistant. Desirably, such compositions and methods employing them can yield coatings that have improved properties. In particular, it would be desirable to improve the durability of the coating, including an improved abrasion resistance of the coating. Furthermore, improving the ease of cleaning of such substrates while using less detergents, water or manual labor, is not only a desire by the end consumer, but has also a positive impact on the environment. Also, it is desired that the coatings show particularly good chemical and solvent resistance. The compositions should be conveniently be applied in an easy and safe way and are compatible with existing manufacturing methods. Preferably, the compositions will fit easily into the manufacturing processes that are practiced to produce the substrates to be treated.

SUMMARY

The present invention provides fluorochemical silane compounds of the formula:

(I)

wherein $R^f$ is a fluorine-containing group;

$R^1$ is a covalent bond, a polyvalent alkylene or arylene group, or combinations thereof, the alkylene groups optionally containing one or more catenary oxygen or nitrogen atoms:

$R^2$ is a silane-containing group derived from a Michael reaction between a fluorochemical amine and an acryloylsilane;

x and y are each independently at least 1, and z is 1 or 2.

In one aspect, this invention relates to chemical compositions comprising one or more compounds and mixtures of compounds having at least one fluorine-containing group and at least one silane-containing moiety, the compounds derived from the Michael reaction between a fluorochemical amine and an acryloylsilane.

Unless otherwise stated, the following terms used in the specification and claims have the meanings given below:

"Alkyl" means a linear or branched, cyclic or acylic, saturated monovalent hydrocarbon radical having from one to about twelve carbon atoms, e.g., methyl, ethyl, 1-propyl, 2-propyl, pentyl, and the like.

"Acryloyl" means an acrylate, thioacrylate or acrylamide.

"Alkylene" means a linear saturated divalent hydrocarbon radical having from one to about twelve carbon atoms or a branched saturated divalent hydrocarbon radical having from three to about twelve carbon atoms, e.g., methylene, ethylene, propylene, 2-methylpropylene, pentylene, hexylene, and the like.

"Alkoxy" means an alkyl having a terminal oxygen atom, e.g. $CH_3$—O—, $C_2H_5$—O—, and the like.

"Aralkylene" means an alkylene radical defined above with an aromatic group attached to the alkylene radical, e.g., benzyl, 1-naphthylethyl, and the like.

"Alkarylene" means an arylene group, with an alkyl groups attached.

"Arylene" means an polyvalent, aromatic radical, such as phenylene, naphthalene, etc.

"Cured chemical composition" means that the chemical composition is dried or solvent has evaporated from the chemical composition at ambient temperature or higher until dryness. The composition may further be crosslinked as result of siloxane bonds formed between the silane compounds.

"Electrophilic fluorochemical compound" means a compound having one or two electrophilic functional groups, such as an acid, acyl halide or ester, and a perfluoroalkyl, perfluoroalkylene, perfluorooxyalkyl or perfluorooxyalkylene group, e.g. $C_4F_9CH_2CH_2CO_2CH_3$, $C_4F_9CO_2H$, $C_2F_5O(C_2F_4O)_3CF_2COCl$, c—$C_6F_{11}CO_2H$, and the like.

"Hard substrate" means any rigid material that maintains its shape, e.g., glass, ceramic, concrete, natural stone, wood, metals, plastics, and the like.

"Oxyalkoxy" has essentially the meaning given above for alkoxy except that one or more oxygen atoms may be present in the alkyl chain and the total number of carbon atoms present may be up to 50, e.g. $CH_3CH_2OCH_2CH_2O$—, $C_4H_9OCH_2CH_2OCH_2CH_2O$—, $CH_3$—O—$(CH_2CH_2O)_{1-100}H$, and the like.

"Oxyalkyl" has essentially the meaning given above for alkyl except that one or more oxygen heteroatoms may be present in the alkyl chain, these heteroatoms being separated from each other by at least one carbon, e.g., $CH_3CH_2OCH_2CH_2$—, $CH_3CH_2OCH_2CH_2OCH(CH_3)CH_2$—, $C_4F_9CH_2OCH_2CH_2$—, and the like.

"Oxyalkylene" has essentially the meaning given above for alkylene except that one or more oxygen heteroatoms may be present in the alkylene chain, these heteroatoms being separated from each other by at least one carbon, e.g., —$CH_2OCH_2O$—, —$CH_2CH_2OCH_2CH_2$—, —$CH_2CH_2OCH_2CH_2CH_2$—, and the like.

"Halo" means fluoro, chloro, bromo, or iodo, preferably fluoro and chloro.

"Perfluoroalkyl" has essentially the meaning given above for "alkyl" except that all or essentially all of the hydrogen atoms of the alkyl radical are replaced by fluorine atoms and the number of carbon atoms is from 1 to about 12, e.g. perfluoropropyl, perfluorobutyl, perfluorooctyl, and the like.

"Perfluoroalkylene" has essentially the meaning given above for "alkylene" except that all or essentially all of the hydrogen atoms of the alkylene radical are replaced by fluorine atoms, e.g., perfluoropropylene, perfluorobutylene, perfluorooctylene, and the like.

"Perfluorooxyalkyl" has essentially the meaning given above for "oxyalkyl" except that all or essentially all of the hydrogen atoms of the oxyalkyl radical are replaced by fluorine atoms and the number of carbon atoms is from 3 to about 100, e.g. $CF_3CF_2OCF_2CF_2$—, $CF_3CF_2O(CF_2CF_2O)_3CF_2CF_2$—, $C_3F_7O(CF(CF_3)CF_2O)_nCF(CF_3)CF_2$—, where s is (for example) from about 1 to about 50, and the like.

"Perfluorooxyalkylene" has essentially the meaning given above for "oxyalkylene" except that all or essentially all of the hydrogen atoms of the oxyalkylene radical are replaced by fluorine atoms, and the number of carbon atoms is from 3 to about 100, e.g., —$CF_2OCF_2$—, or —$[CF_2—CF_2—O]_r$—$[CF(CF_3)—CF_2—O]_s$—; wherein r and s are (for example) integers of 1 to 50.

"Perfluorinated group" means an organic group wherein all or essentially all of the carbon bonded hydrogen atoms are replaced with fluorine atoms, e.g. perfluoroalkyl, perfluorooxyalkyl, and the like.

"Nucleophilic acryloyl compound" means an organic compound with at least one primary or secondary nucleophilic groups per molecule, and at least one acryloyl group, including acrylate and acrylamide groups.

"Michael addition" refers to an addition reaction wherein a nucleophile (such as an fluorochemical amine) undergoes 1,4 addition to an acryloyl group (such as with an acryloylsilane).

DETAILED DESCRIPTION

The present invention provides fluorochemical silane compounds of formula I, described above.

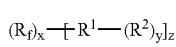

wherein $R_f$ is a fluorine-containing group, including a monovalent perfluoroalkyl-containing group or a perfluorooxyalkyl-containing group group, or a divalent perfluoroalkylene-containing group or a perfluorooxyalkylene-containing group;

$R^1$ is a covalent bond, a polyvalent alkylene or arylene group, or combinations thereof (such as aralkylene or alkarylene), said alkylene groups optionally containing one or more catenary oxygen or nitrogen atoms:

$R^2$ is a silane-containing group derived from the Michael reaction between a fluorochemical amine and an acryloyl silane;

x and y are each independently at least 1, and z is 1 or 2.

With respect to Formula I, $R^2$ is of the following formula:

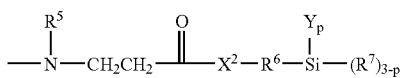

wherein $X^2$ is —O—, —S—, or —$NR^4$—, where $R^4$ is H or $C_1$-$C_4$ alkyl, $R^5$ is H, $C_1$-$C_4$ alkyl, or —$CH_2CH_2$—C(O)—$X^2$—$R^6$—Si$(Y_p)(R^7)_{3-p}$;

$R^6$ is a divalent alkylene group, said alkylene groups optionally containing one or more catenary oxygen atoms;

Y is a hydrolysable group, $R^7$ is a monovalent alkyl or aryl group, p is 1, 2 or 3.

A coating prepared from the coating composition that includes compounds of Formula I includes the compounds per se, as well as siloxane derivatives resulting from bonding to the surface of a preselected substrate and intermolecular crosslinking by siloxane formation. The coatings can also include unreacted or uncondensed "Si—Y" groups. The composition may further contain non-silane materials such as oligomeric perfluorooxyalkyl monohydrides, starting materials and perfluorooxyalkyl alcohols and esters.

Although the inventors do not wish to be bound by theory, compounds of the above Formula I are believed to undergo a condensation reaction with the substrate surface to form a siloxane layer via hydrolysis or displacement of the hydrolysable "Y" groups of Formula II. In this context, "siloxane" refers to —Si—O—Si— bonds to which are attached to compounds of Formula I. In the presence of water, the "Y" groups will undergo hydrolysis to "Si—OH" groups, and further condensation to siloxanes.

In one embodiment, the invention provides a coating composition comprising the compound of Formula I, a solvent, and optionally water and an acid. In another embodiment, the coating composition comprises an aqueous suspension or dispersion of the compounds of Formula I. To achieve good durability for many substrates, such as ceramics, the compositions of the present invention preferably include water. Thus the present invention provides a method of coating comprising the steps of contacting a substrate with a coating composition comprising the compounds of Formula I and a solvent. In another embodiment, compounds of Formula I may be applied by chemical vapor deposition methods to a substrate, particularly for antireflective substrates used in optical applications.

With respect to Formula I, the $R_f$ groups may comprise a monovalent perfluoroalkyl-containing group or a perfluorooxyalkyl-containing group, or a divalent perfluoroalkylene-containing group or a perfluorooxyalkylene-containing group. More particularly, $R_f$ may be represented by Formula III:

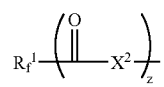

wherein $R_f^1$ is a monovalent perfluoroalkyl or a perfluorooxyalkyl group, or a divalent perfluoroalkylene or a perfluorooxyalkylene group, $X^2$ is —O—, —$NR^4$— or —S—, where $R^4$ is H or $C_1$-$C_4$ alkyl, z is 1 or 2.

The $R_f^1$ groups of Formula III can contain straight chain, branched chain, or cyclic fluorochemical groups or any combination thereof. The $R_f^1$ groups can be mono- or divalent, and can optionally contain one or more catenary oxygen atoms in the carbon-carbon chain so as to form a carbon-oxygen-carbon chain (i.e. a perfluorooxyalkylene group). Fully-fluorinated groups are generally preferred, but hydrogen or other halo atoms can also be present as substituents, provided that no more than one atom of either is present for every two carbon atoms.

It is additionally preferred that any $R_f^1$ group contain at least about 40% fluorine by weight, more preferably at least about 50% fluorine by weight. The terminal portion of the monovalent $R_f^1$ group is generally fully-fluorinated, preferably containing at least three fluorine atoms, e.g., $CF_3$—, $CF_3CF_2$—, $CF_3CF_2CF_2$—, $(CF_3)_2N$—, $(CF_3)_2CF$—, $SF_5CF_2$—. In certain embodiments, monovalent perfluoroalkyl groups (i.e., those of the formula $C_nF_{2n+1}$—) or divalent perfluoroalkylene groups (i.e., those of the formula —$C_nF_{2n}$—) wherein n is 2 to 12 inclusive are the preferred $R_f^1$ groups, with n=3 to 5 being more preferred and with n=4 being the most preferred.

Useful perfluorooxyalkyl and perfluorooxyalkylene $R_f^1$ groups correspond to the formula:

wherein

W is F for monovalent perfluorooxyalkyl, and an open valence ("–") for divalent perfluorooxyalkylene $R_f^3$ represents a perfluoroalkylene group, $R_f^4$ represents a perfluoroalkyleneoxy group consisting of perfluoroalkyleneoxy groups having 1, 2, 3 or 4 carbon atoms or a mixture of such perfluoroalkyleneoxy groups, $R_f^5$ represents a perfluoroalkylene group and q is 0 or 1. The perfluoroalkylene groups $R_f^3$ and $R_f^5$ in formula (IV) may be linear or branched and may comprise 1 to 10 carbon atoms, preferably 1 to 6 carbon atoms. A typical monovalent perfluoroalkyl group is $CF_3$—$CF_2$—$CF_2$— and a typical divalent perfluoroalkylene is —$CF_2$—$CF_2$—$CF_2$—, —$CF_2$— or —$CF(CF_3)CF_2$—. Examples of perfluoroalkyleneoxy groups $R_f^4$ include:—$CF_2$—$CF_2$—O—, —$CF(CF_3)$—$CF_2$—O—, —$CF_2$—$CF(CF_3)$—O—, —$CF_2$—$CF_2$—$CF_2$—O—, —$CF_2$—O—, —$CF(CF_3)$—O—, and —$CF_2$—$CF_2$—$CF_2$—$CF_2$—O—.

The perfluoroalkyleneoxy group $R_f^4$ may be comprised of the same perfluorooxyalkylene units or of a mixture of different perfluorooxyalkylene units. When the perfluorooxyalkylene group is composed of different perfluoroalkylene oxy units, they can be present in a random configuration, alternating configuration or they can be present as blocks. Typical examples of perfluorinated poly(oxyalkylene) groups include: —$[CF_2$—$CF_2$—O$]_r$—; —$[CF(CF_3)$—$CF_2$—O$]_s$—; —$[CF_2CF_2$—O$]_r$—$[CF_2O]_r$—, —$[CF_2CF_2CF_2CF_2$—O$]_u$ and —$[CF_2$—$CF_2$—O$]_r$—$[CF(CF_3)$—$CF_2$—O$]_s$—; wherein each of r, s, t and u each are integers of 1 to 50, preferably 2 to 25. A preferred perfluorooxyalkyl group that corresponds to formula (V) is $CF_3$—$CF_2$—$CF_2$—O—$[CF(CF_3)$—$CF_2O]_s$—$CF(CF_3)CF_2$— wherein s is an integer of 2 to 25.

Perfluorooxyalkyl and perfluorooxyalkylene compounds can be obtained by oligomerization of hexafluoropropylene oxide that results in a terminal carbonyl fluoride group. This carbonyl fluoride may be converted into an acid, ester or alcohol by reactions well known to those skilled in the art. The carbonyl fluoride or acid, ester or alcohol derived therefrom may then be reacted further to introduce the desired groups according to known procedures.

The $R^1$ moiety of Formula I between the $R_f$ sfluorine-containing group and the $R^2$ silyl-containing group includes a polyvalent group selected from an alkylene, arylene, or combinations thereof and an optional catenary oxygen, or nitrogen heteroatom, or combinations thereof. $R^1$ can be unsubstituted or substituted with an alkyl, aryl, halo, or combinations thereof. The $R^1$ group typically has no more than 30 carbon atoms. In some compounds, the $R^1$ group has no more than 20 carbon atoms, no more than 10 carbon atoms, no more than 6 carbon atoms, or no more than 4 carbon atoms. For example, $R^1$ can be an alkylene, an alkylene substituted with an aryl group, or an arylene substituted with an alkyl group.

The $R^1$ moiety of Formula I may be derived from an aliphatic or aromatic compound having at least one amino group and at least one nucleophilic functional groups, including amino, hydroxyl and thiols groups. Such compounds may be of the formula

where $R^1$ is a covalent bond, a polyvalent alkylene or arylene group, or combinations thereof, said alkylene groups optionally containing one or more catenary oxygen or nitrogen atoms; each $X^2$ is independently —O—, —S—, or —$NR^5$—, where $R^5$ is H or $C_1$-$C_4$ alkyl, a is at least one, and x+a is at least two. Such compounds include aminopolyols, polyamines, and hydroxyamines.

Useful polyamines include, for example, polyamines having at least two amino groups, wherein the two amino groups are primary, secondary, or a combination thereof. Examples include 1,10-diaminodecane, 1,12-diaminododecane, 9,9-bis(3-aminopropyl)fluorene, 2-(4-aminophenyl)ethylamine, 1,4-butanediol bis(3-aminopropyl)ether, $N(CH_2CH_2NH_2)_3$, 1,8-diamino-p-menthane, 4,4'-diaminodicyclohexylmethane, 1,3-bis(3-aminopropyl)tetramethyldisiloxane, 1,8-diamino-3,6-dioxaoctane, 1,3-bis(aminomethyl)cyclohexane, and polymeric polyamines such as linear or branched (including dendrimers) homopolymers and copolymers of ethyleneimine (that is, aziridine), and the like.

In some embodiments, preferred polyamines include those of the formula:

wherein each $R^8$ represents H, an alkyl group having from 1 to 4 carbon atoms, or an aryl group having from 6 to 10 carbon atoms; and each $R^9$ independently represents an alkylene group having from 2 to 8 carbon atoms; and v is greater than 2, wherein the number of primary and secondary amino groups in the composition is at least 3. It is preferred that at least one of the terminal amine groups are primary amine groups due to the greater reactivity toward the compounds of Formula VII (below).

Examples of useful polyamines include polyamines having at least three amino groups, wherein the three amino groups are primary, secondary, or a combination thereof include $H_2N(CH_2CH_2NH)_2H$, $H_2N(CH_2CH_2NH)_3H$, $H_2N(CH_2CH_2NH)_4H$, $H_2N(CH_2CH_2NH)_5H$, $H_2N(CH_2CH_2CH_2NH)_2H$, $H_2N(CH_2CH_2CH_2NH)_3H$, $H_2N(CH_2CH_2CH_2CH_2NH)_2H$, $H_2N(CH_2CH_2CH_2CH_2CH_2CH_2NH)_2H$, $H_2N(CH_2)_4NH(CH_2)_3NH_2$, $H_2N(CH_2)_3NH(CH_2)_4NH(CH_2)_3NH_2$, $H_2N(CH_2)_3NH(CH_2)_2NH(CH_2)_3NH_2$, $H_2N(CH_2)_2NH(CH_2)_3NH(CH_2)_2NH_2$, $H_2N(CH_2)_3NH(CH_2)_2NH_2$, $C_6H_5NH(CH_2)_2NH(CH_2)_2NH_2$, and $N(CH_2CH_2NH_2)_3$, and polymeric polyamines such as linear or branched (including dendrimers) homopolymers and copolymers of ethyleneimine (i.e., aziridine). Many such compounds can be obtained, or are available, from general chemical suppliers such as, for example, Aldrich Chemical Company, Milwaukee, Wis. or Pfaltz and Bauer, Inc., Waterbury, Conn. It will be understood with respect to the above polyamines, that both the terminal and catenary amines may undergo Michael addition, as will be further described.

In one embodiment, the fluorochemical compounds of Formula I may comprise, in part, the reaction product of a fluorochemical compound having a mono- or difunctional perfluorinated group, and at least one electrophilic functional group. Such compounds include those of the formula:

$$R_f^1\text{—[C(O)—X}^3]_z, \quad \text{(VII)}$$

wherein $R_f^1$ is a monovalent perfluoroalkyl or a perfluorooxyalkyl group, or a divalent perfluoroalkylene or a perfluorooxyalkylene group, z is 1 or 2, and $X^3$ is a halogen atom or $OR^4$, where $R^4$ is H or $C_1$-$C_4$ alkyl, or, i.e. the compounds of Formula V are esters, acids or acyl halides.

The reaction product of a compound of Formula VII with the polyamine of formula $(HR^5N)_aR^1(X^2H)_x$ (V), or $R^8(N(R^8)\text{—}R^9)_xNR^8H$ (VI), will yield an intermediate of the formula;

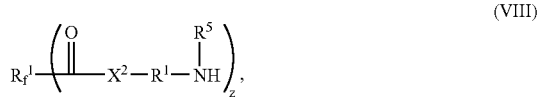

(VIII)

wherein $R_f^1$ is a monovalent perfluoroalkyl or a perfluorooxyalkyl group, or a divalent perfluoroalkylene or a perfluorooxyalkylene group, $X^2$ is —O—, —$NR^4$— or —S—, where $R^4$ is H or $C_1$-$C_4$ alkyl;

$R^1$ is a covalent bond, a polyvalent alkylene or arylene group, or combinations thereof, said alkylene groups optionally containing one or more catenary oxygen or nitrogen atoms;

$R^5$ is $C_1$-$C_4$ alkyl, or $(R_f)_x$—$X^2$—C(O)—$CH_2CH_2$—;

and z is 1 or 2.

The compounds of Formula I may comprise the Michael addition reaction product of fluorochemical amine of Formula VIII and an acryloyl silane compound of the formula

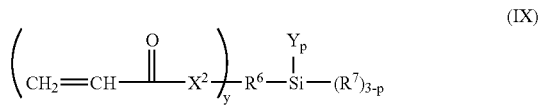

(IX)

wherein $R^6$ is a di- or polyvalent alkylene group, said alkylene groups optionally containing one or more catenary oxygen or nitrogen atoms, and one of more ester, amide, urea or carbamate linkages;

Y is a hydrolysable group, $R^7$ is a monovalent alkyl or aryl group, y is 1 to 4, preferably 1;

p is 1, 2 or 3, preferably 3.

Compounds of Formula IX, where y is greater than 1 may be prepared from the reaction of polyacrylated polyols with an isocyanato silane, such as isocyanatopropyl trimethoxysilane. Useful polyacrylated compounds include those described as "nucleophilic acryloyl compounds" in Assignee's copending application U.S. Ser. No. 11/683,823 filed Feb. 21, 2007, incorporated herein by reference. Alternatively, compounds of Formula IX where y is greater than 1 may be prepared by Michael addition of aminosilanes to a polyacrylated polyol. Useful aminosilanes are also described in U.S. Ser. No. 11/683,823.

The fluorochemical compounds of Formula I may be prepared in a two-step process. The first step is by reaction of electrophilic fluorochemical compounds of Formula VII, such as $C_4F_9C(O)OCH_3$, with polyamine compounds of the formulas V or VI containing at least one amino group and at least one additional nucleophilic group, such as alcohol or primary or secondary amino groups to produce the corresponding fluorochemical amines of Formula VIII. The second step is then to effect Michael addition of the fluorochemical amines of Formula VIII to the acryloyl silane of Formula IX.

In general, the reactive components and a solvent are charged to a dry reaction vessel in immediate succession or as pre-made mixtures. When a homogeneous mixture or solution is obtained a catalyst is optionally added, and the reaction mixture is heated at a temperature, and for a time sufficient for the reaction to occur. Progress of the reaction can be determined by monitoring the IR.

Although no catalyst is generally required for the Michael addition of the aminosilanes to the acryloyl groups, suitable catalysts for the Michael reaction is a base of which the conjugated acid preferably has a pKa between 12 and 14. Most preferably used bases are organic. Examples of such bases are 1,4-dihydropyridines, methyl diphenylphosphane, methyl di-p-tolylphosphane, 2-allyl-N-alkyl imidazolines, tetra-t-butylammonium hydroxide, DBU (1,8-diazabicyclo[5.4.0]undec-7-ene) and DBN (1,5-diazabicyclo[4.3.0]non-5-ene), potassium methoxide, sodium methoxide, sodium hydroxide, and the like. A preferred catalyst in connection with this invention is DBU and tetramethylguanidine. The amount of catalyst used in the Michael addition reaction is preferably between 0.05% by weight and 2% by weight more preferably between 0.1% by weight and 1.0% by weight, relative to solids.

The fluorinated compound of Formula VII is used in an amount sufficient to react with an average of 5 to 50 mole percent of the available amine or alcohol functional groups of the compound $(HR^5N)_aR^1(X^2H)_x$ (V) to produce a compound of Formula VIII. Preferably, the compound of Formula VII is used to react with an average of 10 to 30 mole percent of the groups. The amine groups of Formula VIII are essentially all functionalized by the Michael addition to the acryloylsilane (IX), resulting in a compound having both pendent fluorochemical groups and pendent silane groups.

It will be appreciated that when the polyamines of Formula VI are used, fluorochemical silanes having a plurality of $R_f$ groups and/or silane groups will result. Such compounds may be of the formula:

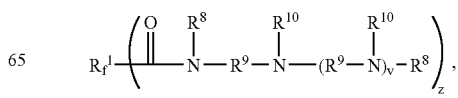

wherein $R_f^1$ is a monovalent perfluoroalkyl or a perfluorooxyalkyl group, or a divalent perfluoroalkylene or a perfluorooxyalkylene group, each $R^8$ represents H, an alkyl group having from 1 to 4 carbon atoms, or an aryl group having from 6 to 10 carbon atoms; and each $R^9$ independently represents an alkylene group having from 2 to 8 carbon atoms; and v is at least 1, preferably greater than 2, z is 1 or 2;

each $R^{10}$ is independently H, an alkyl group having from 1 to 4 carbon atoms, or an aryl group having from 6 to 10 carbon atoms, an $R_f^1$—C(O)— or —CH$_2$CH$_2$C(O)—X$^2$—R$^6$—Si(Y)$_p$(R$^7$)$_{3-p}$, where X$^2$ is —O—, —NR$^4$— or —S—, where R$^4$ is H or C$_1$-C$_4$ alkyl, R$^6$ is a divalent alkylene group, said alkylene groups optionally containing one or more catenary oxygen atoms; Y is a hydrolysable group, R$^7$ is a monovalent alkyl or aryl group, and p is 1, 2 or 3; wherein the compounds contain at least one fluorinated group and at least one silane group.

Compositions according to the present invention may be coated on a substrate and at least partially cured to provide a coated article. In some embodiments, the polymerized coating may form a protective coating that provides at least one of mar resistance, graffiti resistance, stain resistance, adhesive release, low refractive index, and water repellency. Coated articles according to the present invention include, for example, eyeglass lenses, mirrors, windows, adhesive release liners, and anti-graffiti films.

Suitable substrates include, for example, glass (e.g., windows and optical elements such as, for example, lenses and mirrors), ceramic (e.g., ceramic tile), cement, stone, painted surfaces (e.g., automobile body panels, boat surfaces), metal (e.g., architectural columns), paper (e.g., adhesive release liners), cardboard (e.g., food containers), thermosets, thermoplastics (e.g., polycarbonate, acrylics, polyolefins, polyurethanes, polyesters, polyamides, polyimides, phenolic resins, cellulose diacetate, cellulose triacetate, polystyrene, and styrene-acrylonitrile copolymers), and combinations thereof. The substrate may be a film, sheet, or it may have some other form. The substrate may comprise a transparent or translucent display element, optionally having a ceramer hardcoat thereon.

In some embodiments, a coating composition comprising a mixture of the fluorochemical compounds and a solvent is provided. The coating compositions of the present invention comprise solvent suspensions, dispersions or solutions of the fluorochemical compounds of the present invention. When applied as coatings, the coating compositions impart oil- and water-repellency properties, and/or stain-release and stain-resistance characteristics to any of a wide variety of substrates.

The fluorochemical compounds can be dissolved, suspended, or dispersed in a variety of solvents to form coating compositions suitable for use in coating onto a substrate. Generally, the solvent solutions can contain from about 0.1 to about 50 percent, or even up to about 90 percent, by weight non-volatile solids (based on the total weight of the solid components). Coating compositions preferably contain from about 0.1 to about 10 weight percent fluorochemical silane compounds, based on the total solids. Preferably the amount of fluorochemical compounds used in the coating is about 0.1 to about 5 weight percent, most preferably from about 0.2 to about 1 weight percent, of the total solids. Suitable solvents include alcohols, esters, glycol ethers, amides, ketones, hydrocarbons, hydrofluorocarbons, hydrofluoroethers, chlorohydrocarbons, chlorocarbons, and mixtures thereof.

The coating composition may further comprise water and an acid. In one embodiment the method comprises contacting a substrate with a coating composition comprising the silane of Formula I and a solvent, and subsequently contacting the substrate with an aqueous acid.

For ease of manufacturing and for reasons of cost, the compositions of the present invention can be prepared shortly before use by diluting a concentrate of one or more of the compounds of Formula I. The concentrate will generally comprise a concentrated solution of the fluorochemical silane in an organic solvent. The concentrate should be stable for several weeks, preferably at least 1 month, more preferably at least 3 months. It has been found that the compounds can be readily dissolved in an organic solvent at high concentrations.

The coating compositions of this invention optionally contain silsesquioxanes or orthosilicates. The silsesquioxanes may be blended with the coating composition, or alternatively and coating of the compounds of Formula I may be coated on a previously applied coating of the silsesquioxanes. Useful silsesquioxanes include co-condensates of diorganooxysilanes (or hydrosylates thereof) of the formula $R^{10}{}_2Si(OR^{11})_2$ with organosilanes (or hydrosylates thereof) of the formula $R^{10}SiO_{3/2}$ where each $R^{10}$ is an alkyl group of 1 to 6 carbon atoms or an aryl group and $R^{11}$ represents an alkyl radical with 1 to 4 carbon atoms. Preferred silsesquioxanes are neutral or anionic silsesquioxanes, prior to addition to the composition. Useful silsesquioxanes can be made by the techniques described in U.S. Pat. Nos. 3,493,424 (Mohrlok et al.), 4,351,736 (Steinberger et al.), 5,073,442 (Knowlton et al.) 4,781,844 (Kortmann, et al), and 4,781,844, each incorporated herein by reference. Silsequioxanes may be added in amounts of 90 to 99.9 wt. % relative to the total solids.

The silsesquioxanes may be prepared by adding silanes to a mixture of water, a buffer, a surface active agent and optionally an organic solvent, while agitating the mixture under acidic or basic conditions. It is preferable to add the quantity of silane uniformly and slowly in order to achieve a narrow particle size of 200 to 500 Angstroms. The exact amount of silane that can be added depends on the substituent R and whether an anionic or cationic surface-active agent is used. Co-condensates of the silsesquioxanes in which the units can be present in block or random distribution are formed by the simultaneous hydrolysis of the silanes. The amount of tetraorganosilanes, including tetralkoxysilanes and hydrosylates thereof (e.g. of the formula Si(OH)$_4$) present is less than 10 wt. %, preferably less than 5 wt. %, more preferably less than 2 wt. % relative to the weight of the silsesquioxane.

The following silanes are useful in preparing the silsesquioxanes of the present invention: methyltrimethoxysilane, methyltriethoxysilane, methyltriisopropoxyoxysilane, ethyltrimethoxysilane, ethyltriethoxysilane, propyltrimethoxysilane, isobutyltrimethoxysilane, isobutyltriethoxysilane, 2-ethylbutyltriethoxysilane, and 2-ethylbutoxytriethoxysilane.

The composition may be applied to the substrate by conventional techniques such as, for example, spraying, knife coating, notch coating, reverse roll coating, gravure coating, dip coating, bar coating, flood coating, dip coating or spin coating. The composition may be applied to any thickness to provide the desired level of water, oil, stain, and soil repellency. Typically, the composition is applied to the substrate as a relatively thin layer resulting in a dried cured layer having a thickness in a range of from about 40 nm to about 60 nm, although thinner and thicker (e.g., having a thickness up to 100 micrometers or more) layers may also be used. Next, any optional solvent is typically at least partially removed (e.g., using a forced air oven), and the composition is then at least partially cured to form a durable coating.

A preferred coating method for application of a fluorochemical silane of the present invention includes dip coating. A substrate to be coated can typically be contacted with the treating composition at room temperature (typically, about 20 to about 25° C.). Alternatively, the mixture can be applied to substrates that are preheated at a temperature of for example between 60 and 150° C. This is of particular interest for industrial production, where e.g. ceramic tiles can be treated immediately after the baking oven at the end of the production line. Following application, the treated substrate can be dried and cured at ambient or elevated temperature, e.g. at 40 to 300° C. and for a time sufficient to dry. The process may also require a polishing step to remove excess material.

The present invention provides a protective coating on substrate that is relatively durable, and more resistant to contamination and easier to clean than the substrate surface itself. The present invention provides in one embodiment a method and composition for use in preparing a coated article comprising a substrate, preferably a hard substrate, and an antisoiling coating of greater than a monolayer (which is typically greater than about 15 Angstroms thick deposited thereon. Preferably an antisoiling coating of the present invention is at least about 20 Angstroms thick, and more preferably, at least about 30 Angstroms thick. Generally, the thickness of the coating is less than 10 micrometers, preferably less than 5 micrometers. The coating material is typically present in an amount that does not substantially change the appearance and optical characteristics of the article.

The compounds of claim 1 are particularly suited for preparing antisoiling coatings for antireflective substrates, such as those used in ophthalmic lenses. The coating can be provided by vapor deposition, or by dip-coating, flood coating, curtain coating, spin-coating, bar-coating or other solvent- or aqueous-borne methods.

Antireflective coatings may include one or more layers of material disposed on a transparent (i.e., light transmissive) substrate, such as glass, quartz, or organic polymeric substrates, including polymethyl methacrylate, polystyrene, polyvinyl chloride, polythiourethane, polyethylene, polypropylene, polycarbonate, polyimide, and polyesters, particularly polyethylene terephthalate. The simplest antireflective coating is a single layer of a transparent material having a refractive index less than that of the substrate on which it is disposed. Multilayer antireflective coatings include two or more layers of dielectric material on a substrate, wherein at least one layer has a refractive index higher than the refractive index of the substrate. They are often referred to as antireflective film stacks.

The antireflective coating may be provided by a wide variety of materials. Preferably, the antireflective coating is provided by a thin metal oxide film, and more preferably, by a thin sputter coated metal oxide film. Herein, "metal oxide" includes oxides of single metals (including metalloids) as well as oxides of metal alloys. Preferred metal oxides include silicon oxides, which may be depleted of oxygen (i.e., wherein the amount of oxygen in the oxide is less than the stoichiometric amount). Preferably, the metal oxide film on the outermost surface includes silicon oxides ($SiO_x$, wherein x is no greater than 2), although other suitable materials include oxides of tin, titanium, niobium, zinc, zirconium, tantalum, yttrium, aluminum, cerium, tungsten, bismuth, indium, and mixtures thereof. Specific examples include $SiO_2$, $SnO_2$, $TiO_2$, $Nb_2O_5$, $ZnO$, $ZrO_2$, $Ta_2O_5$, $Y_2O_3$, $Al_2O_3$, $CeO_2$, $WO_3$, $Bi_2O$, $In_2O_3$, and ITO (indium tin oxide), as well as combinations and alternating layers thereof.

Sputter coated metal oxide films are preferred over thermally evaporated films because sputter coated films have higher densities and are harder, smoother, and more stable than thermally evaporated films. Although such sputter coated metal oxide films are relatively porous and consist of clusters of particles with diameters on the order of about 5 nanometers to about 30 nanometers as measured by atomic force microscopy, they are sufficiently impermeable to water and gases that can alter their mechanical, electrical, and optical properties.

Suitable transparent substrates include glass and transparent thermoplastic materials such as poly(meth)acrylate, polycarbonate, polythiourethanes, polystyrene, styrene copolymers, such as acrylonitrile-butadiene-styrene copolymer and acrylonitrile-styrene copolymer, cellulose esters, particularly cellulose acetate and cellulose acetate-butyrate copolymer, polyvinyl chloride, polyolefins, such as polyethylene and polypropylene, polyimide, polyphenyleneoxide, and polyesters, particularly polyethylene terephthalate. The term "poly(meth)acrylate" (or "acrylic") includes materials commonly referred to as cast acrylic sheeting, stretched acrylic, poly(methylmethacrylate) "PMMA," poly(methacrylate), poly(acrylate), poly(methylmethacrylate-co-ethylacrylate), and the like. The substrate thickness can vary, however, for flexible organic films it typically ranges from about 0.1 mm to about 1 mm. Additionally, the organic polymeric substrate can be made by a variety of different methods. For example, the thermoplastic material can be extruded and then cut to the desired dimension. It can be molded to form the desired shape and dimensions. Also, it can be cell cast and subsequently heated and stretched to form the organic polymeric substrate.

The substrate on which the antireflective coating is deposited may include a primed surface. The primed surface can result from the application of a chemical primer layer, such as an acrylic layer, or from chemical etching, electronic beam irradiation, corona treatment, plasma etching, or coextrusion of adhesion promoting layers. Such primed substrates are commercially available. For example, a polyethylene terephthalate substrate primed with an aqueous acrylate latex is available from Imperial Chemical Industries Films, Hopewell, N.C.

Thus, the present invention provides an antisoiling composition for antireflective substrates, and method of depositing an antisoiling composition on an antireflective substrate comprising vaporizing an antisoiling composition and depositing the antisoiling composition onto an antireflective substrate. An antireflective substrate is any transparent substrate that is part of an antireflective film stack, or any transparent substrate having a surface that is covered in whole or in part with an antireflective composition. The antireflective composition is preferably an antireflective metal oxide, metal fluoride, metal nitride, metal sulfide, or the like. More preferably the antireflective composition is an antireflective metal oxide, and most preferably, the antireflective composition is a sputter coated antireflective metal oxide film (preferably comprising silicon oxides). An antisoiling composition of the present invention renders a surface more resistant to contamination, as by skin oils from fingerprints, for example. It also renders the surface easier to clean, preferably either with dry wiping or with water and detergent. Furthermore, it causes little or no disruption of the optical properties of the surface to which it is applied, particularly the antireflective surface of a film stack. That is, the antisoiling coating of the present invention does not significantly increase the reflectivity of the film stack.

The articles produced by the method of the present invention include a substrate, such as glass or an organic polymeric substrate, optionally having a primed surface on which is coated an optional adhesion enhancing coating, an antireflective composition, preferably, a multilayer film stack, and an antisoiling composition comprising the compounds of Formula I.

The overall thickness of the antisoiling composition results from balancing the desire for a thick coating for enhancing antisoiling and durability properties with the desire for a thin coating for maintaining the antireflective properties of the antireflective substrate. Typically, the overall coating thickness of an antisoiling composition of the present invention is from about 20 to 500 angstroms, more preferably from about 40 to 100 angstroms. In another aspect, the antisoiling composition is preferably deposited as a monolayer.

The conditions under which the antisoiling composition is vaporized may vary according to the structure and molecular weight of the antisoiling composition. In one aspect of the invention, it is preferred that the vaporizing may take place at pressures less than about 0.01 mmHg. In another aspect of the invention, the vaporizing may take place at temperatures of at least about 80° C.

In another embodiment of the present invention, the vaporizing comprises placing the antisoiling composition and the antireflective substrate into a chamber, heating the chamber (containing the antisoiling composition), and decreasing the pressure in the chamber, suing vapor deposition methods known in the art. The invention also provides a method wherein the chamber is heated prior to placing the antisoiling composition and antireflective substrate into the chamber. Alternatively, the antisoiling composition is placed in a first chamber and the antireflective coated ophthalmic lens is placed in a second chamber connected to the first chamber such that vaporized antisoiling composition from the first chamber can deposit on the antireflective coated ophthalmic lens in the second chamber. In another aspect of the invention, the second chamber may remain at ambient temperature while the first chamber is heated. Useful vacuum chambers and equipment are known in the art. One commercially available unit is the 900 DLS available from Satis Vacuum of America, Grove Port, Ohio.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

All parts, percentages, ratios, etc. in the examples and the rest of the specification are by weight, unless noted otherwise. Solvents and other reagents used were obtained from Aldrich Chemical Company, Milwaukee, Wis. unless otherwise noted.

EXPERIMENTAL

Glossary List:

Unless otherwise noted, as used in the examples, "HFPO—" refers to the end group $F(CF(CF_3)CF_2O)_aCF(CF_3)$— of the methyl ester $F(CF(CF_3)CF_2O)_aCF(CF_3)C(O)OCH_3$, wherein a averages from 4-20, which can be prepared according to the method reported in U.S. Pat. No. 3,250,808 (Moore et al.), the disclosure of which is incorporated herein by reference, with purification by fractional distillation.

HFPO dimethylester:

$CH_3O(O)CCF(CF_3)(OCF_2CF(CF_3))_bOCF_2CF_2CF_2CF_2O(CF(CF_3)CF_2O)_cCCF(CF_3)COOCH$, also referred to as $H_3CO(O)C$—HFPO—$C(O)OCH_3$ or HFPO—$(C(O)OCH_3)_2$, in which b+c average from about 4 to 15 can be prepared using $FC(O)CF_2CF_2C(O)F$ as an starting material according to the method reported in U.S. Pat. No. 3,250,807 (Fritz, et al.) which provides the HFPO oligomer bis-acid fluoride, followed by methanolysis and purification by removal of lower boiling materials by fractional distillation as described in U.S. Pat. No. 6,923,921 (Flynn, et. al.). HFPO—$CONHCH_2CH_2OCOCH=CH_2$ (HFPO-AEA) was prepared as described in Preparations 31A of U.S. 2006/0216500 (Klun et al.).

3-acryloxypropyltrimethoxysilane was obtained from Gelest, Inc. Morrisville, Pa. Note the following $CH_2=CHC(O)O(CH_2)_3Si(OCH_3)_3$ was purchased from VWR international, Inc, West Chester, Pa.

$NH_2CH_2CH_2$—NH—$CH_2CH_2$—NH—$CH_2CH_2$—$NH_2$ was purchased from VWR international, Inc, West Chester, Pa.

$NH(CH_3)$—$(CH_2)_3$—$NH_2$ was purchased from VWR international, Inc, West Chester, Pa.

Test Methods

Nuclear Magnetic Resonance (NMR)

$^1H$ and $^{19}F$ NMR spectra were run on a Varian UNITYplus 400 Fourier transform NMR spectrometer (available from Varian NMR Instruments, Palo Alto, Calif.).

IR Spectroscopy (IR)

IR spectra were run on a Thermo-Nicolet, Avatar 370 FTIR, obtainable from Thermo Electron Corporation, Waltham, Mass.

Treatment of Ophthalmic Lenses by Chemical Vapor Deposition (CVD):

A clean lens was treated with each of selected fluorochemical silanes of this invention in a vapor deposition chamber under 3×10 −6 torr pressure. The vaporization temperature for the silanes ranged from 350-500° C. The coating was then cured under ambient conditions.

The polycarbonate AirWear Crizal™ anti-reflective lens blanks (obtained from Essilor USA, St. Petersburg, Fla.) are believed to have a scratch resistant hard coat, an antireflective (AR) coating and hydrophobic top coat. The AR coating is believed to comprise a four layer CVD coating comprising zirconium oxide/silicon oxide/zirconium oxide/silicon oxide.

To remove the hydrophobic topcoat, and allowed deposition of the fluorochemical silanes of the invention, the commercial lens blanks were rinsed with isopropanol and dried with an air blower, then exposed to vacuum plasma for 3 minutes in a Harrick PDC-32G Cleaner/Sterilizer (Harrick Scientific Corp. Pleasantville, N.Y.).

Drain Time Test:

For this test the drain time of a liquid from a treated ophthalmic lens was determined using a dip coater. The treated lenses are dipped into and subsequently withdrawn from a liquid (either oleic acid or isopropanol (IPA)). The withdrawal speed for the test was 5 cm (2 inches) per second. The time needed for the liquid to drain completely was measured with a timer.

Table 1 exhibit measured drain times for comparison of selected CVD and dip coated polycarbonate lenses for isopropanol and oleic acid. According to the data, in general, the CVD coating of the lenses results in shorter drain times for both IPA and oleic acid than the dip coating. Drain time is used to measure the slipperiness of a treated lens, the shorter the time needed for the liquid to drain completely, the more slippery of the surface. Faster draining of the liquid is also an indication of better hydrophobic an oleophobic surface.

Static and Dynamic Contact Angles:

The static, advancing and receding contact angle test provides a quick and precise prediction of the surface properties of coating materials. The contact angles for treated lenses (after drying and curing) were measured using a Kruss G120 and AST VCA 2500 XE Video Contact Angle System (AST Products, Inc.), both equipped with a computer for control and date process. The data was generated for both water and n-hexadecane. Table 2 summarizes the static, advancing and receding contact angles for lenses treated with various silanes using both CVD and dip coating processes. Measured contact angles were high for all treated lenses, although, in general, the lenses treated by dip coating resulted in slightly higher contact angles.

Hysteresis of Treated Lenses:

The difference between the maximum (advancing) and minimum (receding) contact angle values is called the contact angle hysteresis, which characterizes surface heterogeneity, roughness and mobility. It is possible that the easy cleaning performance of a coated surface is correlated to the contact angle hysteresis. The higher receding contact angle would help to remove the staining liquid from the treated surface. Thus, the smaller the contact angle hysteresis, the better the performance. The Table 1 lists the hysteresis of several treated lenses.

Durability Test:

The durability silane treatments on lenses were determined in the following manner: The treated lenses were subjected to an abrasion test using a Lens Eraser Abrasion Tester (obtained from Colts Laboratories, Inc., Clearwater, Fla.) and a 3M High Performance Cloth™ (Scotch-Brite™ Microfiber Dusting Cloth, obtained from 3M Company, St. Paul, Minn.) under a 2.27 kg (5 lbs.) load for 500 cycles. Then the contact angles for the treated lenses following the abrasion test were measured again using the method described above. Table 2 shows the contact angle data of the treated lenses after the abrasion resistance test. Table 3 shows the contact angle data for the lenses treated by dipcoat, before and after abrasion resistance test respectively.

Adhesion and Edging Testing:

This test is run to determine the ability of a pad to hold a lens in position in the edger during the cutting operation, which consists in machining the rim or periphery of the lens to conform it to the required dimensions of a frame. Sealing paper from one side of the Leap Pad III (available from the 3M Company, St Paul, Minn.) was peeled and applied to the center of the coated lens, which is firmly affixed in the torque tool with 30 cm (12¼") bar.

A block, the device that holds the lens in position while the lens rotates, was applied to the other side of the Leap Pad III. The torque tool with pad and lens was inserted into the edger (alignment of block flanges into blocker is critical) and firmly pressed with 2.86 atmospheres (42 psi) pressure on the pad. The tip of the torque tool was lined up with zero degree on the torque scale. A horizontal force of 0.45 kilogram (6 lbs) was applied using spring scale for one minute and the new position of torque tool on the torque scale was recorded as the degree from the zero position. If the torque degree is less than or equal to 5, it is considered to have adequate adhesion and ability to hold the lens in the edging process.

The test results for the silane treatments of this invention are shown in the Table 2. The torque degree for comparative Alize™ lens blank (obtained from Essilor USA) was >15, which requires a special temporary coating for the edging process (see WO 01/68384 and US2004/0253369). The new silane treatments described in this invention all pass this torque test. If the CVD coated lens of FC silanes was first washed with isopropanol before the torque test, the adhesion was improved and passed the test. Therefore, the silane treatments of this invention do not require a special temporary coating for the edging process.

Preparative Example 1

Synthesis of HFPO—CO—NH—CH$_2$)$_3$NH(CH$_3$)

A 1 L 1 necked round bottom flask equipped with magnetic stir bar and inlet adapter was charged with HFPO—C(O)OCH$_3$ (MW: 1211, 300 g, 0.2477 moles) and H$_2$N(CH$_2$)$_3$NHCH$_3$ (MW: 88.15, 21.84 g, 0.2477 moles) and stirred under nitrogen at 50° C. for 16 h. The reaction was terminated as FTIR analysis confirmed the disappearance of a peak correlated with HFPO—C(O)OCH$_3$ (~1790 cm$^{-1}$) along with the appearance of a peak correlated with the desired amide (~1710 cm$^{-1}$). MeOH was removed from the product by heating in a rotary evaporator at 75° C. The product was used as such for the next step.

Example 1

Synthesis of 1. HFPO—CO—NH—(CH$_2$)$_3$N(CH$_3$)—(CH$_2$)$_2$CO—O—(CH$_2$)$_3$—Si(OCH$_3$)$_3$ A 100 mL 3 necked round bottom flask was equipped with magnetic stir bar, N$_2$ inlet and reflux condenser was charged with HFPO—CO—NH—(CH$_2$)$_3$NH—CH$_3$ (5 g, 0.00395 moles) under N$_2$ atmosphere. 3-acryloylpropyltrimethoxysilane (0.923 g, 0.00395 moles) was added drop wise to the flask over a period of 15 minutes. The reaction was exothermic, and was stirred for 30 minutes at room temperature, then heated at 55° C. for 12 hours to yield a clear viscous oil.

Preparative Example 2

Synthesis of HFPO—CO—NHCH₂CH₂—NH—CH₂CH₂—NH—CH₂CH₂—NH—CO—HFPO

A 100 mL 3 necked round bottom flask was equipped with magnetic stir bar, N₂ inlet and reflux condenser was charged with HFPO—COOMe (2 g, 0.001579 moles) and NH₂CH₂CH₂—NH—CH₂CH₂—NH—CH₂CH₂—NH₂ (0.1152 g, 0.0007895 moles) underN₂ atmosphere. The reaction mixture was heated at 75° C. for 12 h. The reaction was monitored by IR and after the disappearance of ester peak, and the clear viscous oil obtained was used as such for the next step.

Example 2

Synthesis of 2.HFPO—CO—NH—CH₂CH₂—N[(CH₂)₂CO—O—(CH₂)₃—Si(OCH₃)₃)]—CH₂CH₂—N[(CH₂)₂CO—O—(CH₂)3—Si(OCH₃)₃]—CH₂CH₂—NH—CO—HFPO A 100 mL 3 necked round bottom flask was equipped with magnetic stir bar, N₂ inlet and reflux condenser was charged with HFPO—CO—NH—CH₂CH₂—NH—CH₂CH₂—NH—CH₂CH₂—NH—CO—HFPO (10 g, 0.0038 moles) under N₂ atmosphere. 3-acryloylpropyltrimethoxysilane (1.79 g, 0.00763 moles) was added dropwise to the flask over a period of 15 minutes. The reaction was exothermic, and was stirred for 30 minutes at room temperature, then heated at 55° C. for 12 h. The clear viscous oil obtained was submitted for CVD and analysis.

Preparative Example 3

Synthesis of HFPO—(C(O)NH(CH₂)₃NHCH₃)₂

A 200 mL 1 necked round bottom flask equipped with magnetic stir bar and inlet adapter was charged with HFPO—(C(O)OCH₃)₂ (MW: 2400, 100 g, 0.0417 moles) and H₂N(CH₂)₃NHCH₃ (MW: 88.15, 8.82 g, 0.1000 moles) and stirred under nitrogen at 75° C. for 24 h. The reaction was terminated as FTIR analysis confirmed the disappearance of a peak correlated with HFPO—(C(O)OCH₃)₂ (~1790 cm⁻¹) along with the appearance of a peak correlated with the desired amide (~1710 cm⁻¹). The product was washed successively with three 110 g aliquots of dichloromethane, discarding dichloromethane following separation each time, to remove excess H₂N(CH₂)₃NHCH₃. The ¹H-NMR of HFPO—(C(O)NH(CH₂)₃NHCH₃)₂ showed the desired product was free of excess H₂N(CH₂)₃NHCH₃.

Example 3

Synthesis of 3. HFPO—(C(O)—NH—(CH₂)₃N(CH₃)(CH₂CH₂C(O)O(CH₂)₃Si(OCH₃)₃)₂

A 100 mL 1 necked round bottom flask equipped with magnetic stir bar and inlet adapter was charged with HFPO—(C(O)—NH—(CH₂)₃NHCH₃)₂ (MW: 2512, 15 g, 0.0060 moles) and stirred under dry air at 65° C. for 10 minutes. CH₂=CHC(O)O(CH₂)₃Si(OCH₃)₃ (MW: 233.96, 2.79 g, 0.0119 moles) was added dropwise to the flask over a period of five minutes. The temperature was reduced to 55° C. and stirred for 24 h. The ¹H-NMR of HFPO(C(O)NH(CH₂)₃N(CH₃)CH₂CH₂C(O)O(CH₂)₃Si(OCH₃)₃)₂ confirmed the desired product.

TABLE 1

Data for CVD Coated Ophthalmic Lenses

| | Initial Contact Angle | | | | | | | | Drain Time | |
|---|---|---|---|---|---|---|---|---|---|---|
| | Static | | Adv | | Rec | | Hyst | | | |
| Ex | Water | HD | Water | HD | Water | HD | Water | HD | OA | IPA |
| 1 | 111.4 | 71.7 | 123.3 | 75.8 | 101.5 | 67.4 | 21.8 | 8.4 | 15.0 | 2.9 |
| 2 | 108.9 | 70.3 | 123.2 | 74.2 | 85.8 | 62.3 | 37.4 | 11.9 | 42.2 | 7.6 |
| 3 | 104.3 | 65.6 | 114.4 | 70 | 70.4 | 55.2 | 44 | 14.8 | 33.2 | 8.7 |

Ex—Example, HD—Hexadecane, OA—Oleic acid, IPA—Isopropyl alcohol

TABLE 2

Durability Data

| | Contact angle after Durability test | | | | | | Edging Test Leap Pad III |
|---|---|---|---|---|---|---|---|
| | Static | | Adv | | Rec | | (Torque |
| Ex | Water | HD | Water | HD | Water | HD | degree) |
| 1 | 94.2 | 60.3 | 99.6 | 63 | 55.7 | 35.7 | 3 |
| 2 | 85.5 | 50.5 | 91.5 | 50.8 | 42.7 | 30.1 | 4 |
| 3 | 89.1 | 59.2 | 93.1 | 60.8 | 49.1 | 37.4 | 3 |

Ex—Example, HD—Hexadecane, OA—Oleic acid, IPA—Isopropyl alcohol

The invention claimed is:

1. A compound of the formula

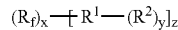

wherein $R_f$ is a fluorine-containing group;

$R^1$ is a covalent bond, a polyvalent alkylene or arylene group, or combinations thereof, said alkylene groups optionally containing one or more catenary oxygen or nitrogen atoms;

$R^2$ is of the formula:

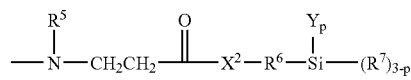

wherein

X is —O—, —S—, or —NR⁴—, where R⁴ is H or C₁-C₄ alkyl;

R⁵ is H, C₁-C₄ alkyl, or —CH₂CH₂—C(O)—X²—R⁶—Si(Y_p)(R⁷)_{3-p};

R⁶ is a divalent alkylene group, said alkylene groups optionally containing one or more catenary oxygen atoms;

Y is a hydrolysable group;

R⁷ is a monovalent alkyl or aryl group;

p is 1, 2 or 3; and x and y are each independently at least 1, and z is 1 or 2.

2. The compound of claim 1, where $R_f$ is of the formula:

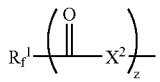

wherein $R_f^1$ is a monovalent perfluoroalkyl or a perfluorooxyalkyl group, or a divalent perfluoroalkylene or a perfluorooxyalkylene group, X² is —O—, —NR⁴—, or —S—, where R⁴ is H or C₁-C₄ alkyl, z is 1 or 2.

3. The compounds of claim 1 wherein R² is derived from a Michael reaction between a fluorine-containing amine and an acryloylsilane.

4. The compounds of claim 1 wherein $R_f$ comprises a fluorine-containing groups selected from monovalent perfluoroalkyl and perfluorooxyalkyl groups, and divalent perfluoroalkylene and perfluorooxyalkylene groups.

5. The compound of claim 2 wherein $R_f^1$ is a monovalent perfluorooxyalkyl group, or a divalent perfluorooxyalkylene group comprising one or more perfluorinated repeating units selected from the group consisting of —(C_nF_{2n}O)—, —(CF(Z)O)—, —(CF(Z)C_nF_{2n}O)—, —(C_nF_{2n}CF(Z)O)—, —(CF₂CF(Z)O)—, and combinations thereof, wherein n is 1 to 4 and Z is a perfluoroalkyl group, a perfluoroalkoxy group, or perfluorooxyalkyl group.

6. The compounds of claim 2 wherein $R_f^1$ comprises a group of the formula

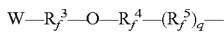

wherein

W is F for monovalent perfluorooxyalkyl, and an open valence ("–") for divalent perfluorooxyalkylene;

$R_f^3$ represents a perfluoroalkylene group, $R_f^4$ represents a perfluoroalkyleneoxy group consisting of perfluorooxyalkylene groups having 1, 2, 3 or 4 carbon atoms or a mixture of such perfluorooxyalkylene groups, $R_f^5$ represents a perfluoroalkylene group, and q is 0 or 1.

7. The compound of claim 4 wherein said perfluorooxyalkylene group is selected from one or more of —[CF₂—CF₂—O]_r—; —[CF(CF₃)—CF₂—O]_r—; —[CF₂CF₂—O]_t—[CF₂O]_t—, —[CF₂CF₂CF₂—O]_u— and —[CF₂—CF₂—O]_r—[CF(CF₃)—CF₂—O]_s—; wherein each of r, s, t and u each are integers of 1 to 50.

8. The compounds of claim 1 wherein $R_f$ comprises a divalent perfluorooxyalkylene group and z is 2.

9. The compound of claim 2 wherein $R_f$ is a monovalent perfluorooxyalkyl group and z is 1.

10. The compound of claim 1, wherein Y is a halogen, a C₁-C₄ alkoxy group, or a C₁-C₄ acyloxy group.

11. The compounds of claim 2 wherein the molar ratio of silane groups to $R_f$ groups is greater than 1:1.

12. The compounds of claim 3 wherein the fluorine-containing amine is of the formula:

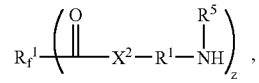

where $R_f^1$ is a monovalent perfluoroalkyl or a perfluorooxyalkyl group, or a divalent perfluoroalkylene or a perfluorooxyalkylene group, X² is —O—, —NR⁴—, or —S—, where R⁴ is H or C₁-C₄ alkyl;

R¹ is a covalent bond, a polyvalent alkylene or arylene group, or combinations thereof, said alkylene groups optionally containing one or more catenary oxygen or nitrogen atoms;

R⁵ is C₁-C₄ alkyl, or $(R_f)_x$—X²—C(O)—CH₂CH₂—; and z is 1 or 2.

13. The compounds of claim 1, derived from an acryloylsilane of the formula:

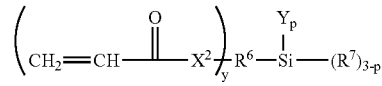

wherein

R⁶ is a di- or polyvalent alkylene group, said alkylene groups optionally containing one or more catenary oxygen or nitrogen atoms, and one of more ester, amide, urea or carbamate linkages;

X² is —O—, —NR⁴— or —S—, where R⁴ is H or C₁-C₄ alkyl;

Y is a hydrolysable group,

R⁷ is a monovalent alkyl or aryl group, y is 1 to 4;

p is 1, 2 or 3.

14. A coating composition comprising at least one compound of claim 1 and a solvent.

15. The coating composition of claim 14 further comprising a silsesquioxane.

16. A compound of claim 1 of the formula:

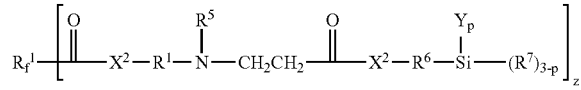

wherein $R_f^1$ is a monovalent perfluoroalkyl or a perfluorooxyalkyl group, or a divalent perfluoroalkylene or a perfluorooxyalkylene group, X² is —O—, —NR⁴— or —S—, where R⁴ is H or C₁-C₄ alkyl;

R⁵ is C₁-C₄ alkyl, or —CH₂CH₂C(O)—X²—R⁶—Si(Y_p)(R⁷)_{3-p} or $(R_f)_x$—X²—C(O)—CH₂CH₂—;

$R^6$ is a divalent alkylene group, said alkylene groups optionally containing one or more catenary oxygen atoms;
Y is a hydrolysable group,
$R^7$ is a monovalent alkyl or aryl group,
p is 1, 2 or 3, and
z is 1 or 2.

17. A compound of claim 1 of the formula:

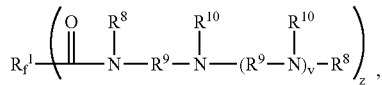

wherein
$R_f^1$ is a monovalent perfluoroalkyl or a perfluorooxyalkyl group, or a divalent perfluoroalkylene or a perfluorooxyalkylene group,
each $R^8$ represents H, an alkyl group having from 1 to 4 carbon atoms, or an aryl group having from 6 to 10 carbon atoms; and
each $R^9$ independently represents an alkylene group having from 2 to 8 carbon atoms; and v is at least 1,
z is 1 or 2;
each $R^{10}$ is independently H, an alkyl group having from 1 to 4 carbon atoms, or an aryl group having from 6 to 10 carbon atoms, an $R_f^1$—C(O)— or —CH$_2$CH$_2$C(O)—X$^2$—R$^6$—Si(Y)$_p$(R$^7$)$_{3-p}$, where X$^2$ is —O—, —NR$^4$— or —S—, where $R^4$ is H or $C_1$-$C_4$ alkyl, $R^6$ is a divalent alkylene group, said alkylene groups optionally containing one or more catenary oxygen atoms; Y is a hydrolysable group, $R^7$ is a monovalent alkyl or aryl group, and p is 1, 2 or 3; and
wherein the compounds contain at least one fluorinated group and at least one silane group.

18. The compounds of claim 17 wherein the number of $R_f^1$ groups is greater than the number of silane groups.

19. The compounds of claim 17 wherein the number of silane groups is greater than the number of $R_f^1$ groups.

20. A method of coating comprising the step of contacting a substrate with the coating composition of claim 14.

* * * * *

UNITED STATES PATENT AND TRADEMARK OFFICE
CERTIFICATE OF CORRECTION

PATENT NO.       : 7,335,786 B1
APPLICATION NO.  : 11/693510
DATED            : February 26, 2008
INVENTOR(S)      : Suresh S. Iyer It is certified that error appears in the above-identified patent and that said Letters Patent is hereby corrected as shown below:

Column 1,
Line 51, delete "$R^f$" and insert -- $R_f$ --, therefor.

Column 2,
Line 42, delete "$CH_3–O–$" and insert -- $CH_3O$ --, therefor.

Column 3,
Line 6, delete "$CF_2O)_nCF$" and insert -- $CF_2O)_sCF$ --, therefor.

Column 5,
Line 48, delete "$CF_2–O]_s;$" and insert -- $CF_2–O]_s–;$ --, therefor.

Line 63, delete "sfluorine" and insert -- fluorine --, therefor.

Column 10,
Line 53, delete "$S1(OH)_4)$" and insert -- $Si(OH)_4)$ --, therefor.

Column 14,
Line 15, delete "$O)CCF$" and insert -- $O)_CCF$ --, therefor.

Line 54, delete "3x10 -6" and insert -- $3 \times 10^{-6}$ --, therefor.

Column 17,
Line 14, delete "$underN_2$" and insert -- under $N_2$ --, therefor.

Line 37, delete "2.HFPO" and insert -- 2. HFPO --, therefor.

Line 39, delete "$(CH_2)3$" and insert -- $(CH_2)_3$ --, therefor.

Column 19,
Line 2, in claim 1, delete "X" and insert -- $X^2$ --, therefor.

Line 60, in claim 7, delete "$CF_2–O]–;$" and insert -- $CF_2–O]_s–;$ --, therefor.

Column 20,
Line 57, in claim 16, after "$]_z$" insert -- , --.

UNITED STATES PATENT AND TRADEMARK OFFICE
CERTIFICATE OF CORRECTION

PATENT NO. : 7,335,786 B1
APPLICATION NO. : 11/693510
DATED : February 26, 2008
INVENTOR(S) : Suresh S. Iyer It is certified that error appears in the above-identified patent and that said Letters Patent is hereby corrected as shown below:

Column 22,
Line 17, in claim 18, delete "$R^{f1}$" and insert -- $R_f^1$. --, therefor.

Signed and Sealed this

Second Day of December, 2008

JON W. DUDAS
*Director of the United States Patent and Trademark Office*